US00PP26062P3

(12) United States Plant Patent
Bodapati et al.

(10) Patent No.: US PP26,062 P3
(45) Date of Patent: Nov. 10, 2015

(54) ***PONGAMIA* TREE NAMED 'K128B'**

(50) Latin Name: ***Pongamia pinnata* (L) Pierre**
Varietal Denomination: K128b

(71) Applicant: TERVIVA BIOENERGY, Oakland, CA (US)

(72) Inventors: Naidu Bodapati, Oakland, CA (US); Marshall Mackay, Oakland, CA (US)

(73) Assignee: Terviva Bioenergy, Oakland, CA (US)

( * ) Notice: Subject to any disclaimer, the term of this patent is extended or adjusted under 35 U.S.C. 154(b) by 0 days.

(21) Appl. No.: 13/987,125

(22) Filed: Jul. 1, 2013

(65) Prior Publication Data

US 2015/0020250 P1 Jan. 15, 2015

(51) Int. Cl.
*A01H 5/00* (2006.01)

(52) U.S. Cl.
USPC ..... Plt./216

(58) Field of Classification Search
USPC ..... Plt./216
CPC ..... A01H 5/00
See application file for complete search history.

(56) References Cited

PUBLICATIONS

U.S. Appl. No. 13/987,126, filed Jul. 1, 2013, Bodapati et al.
U.S. Appl. No. 13/987,127, filed Jul. 1, 2013, Bodapati et al.

*Primary Examiner* — Kent L Bell
(74) *Attorney, Agent, or Firm* — Dentons US LLP

(57) ABSTRACT

'K128b' is a new *Pongamia* tree distinguished by having consistent and abundant production of seed pods, coupled with the high oil content of the seeds.

7 Drawing Sheets

Latin name of the genus and species of the plant claimed: *Pongamia pinnata* (L) Pierre.

Cultivar denomination: 'K128b'.

BACKGROUND OF THE INVENTION

The invention relates to a new and distinct cultivar of *Pongamia* tree (*Pongamia pinnata* (L) Pierre) named 'K128b'. 'K128b' was discovered by the inventors growing in an urban cultivated area in southeastern Queensland, Australia, wherein it and neighboring trees are grown for shade and other landscape amenities. The parentage of this tree is unknown, as is typical for trees cultivated in landscape plantings of this type.

'K128b' has been reproduced asexually through vegetative cuttings.

'K128b' has not been made publicly available more than one year prior to the filing date of this application.

SUMMARY OF THE INVENTION

A new and distinct variety of *Pongamia* tree (*Pongamia pinnata* (L) Pierre), named 'K128b', which is distinctly characterized by a dense, spreading crown, and by regularly (e.g. annually or nearly so) bearing copious quantities of fruit pods containing seeds with high seed-oil content (38.5%, dry-weight basis). Pods tend to appear in dense clusters. 'K128b' demonstrates excellent vigor and is reasonably resistant to insect and disease pests.

The original tree of 'K128b' was initially identified and selected primarily on the basis of its consistent production of abundant seed pods, coupled with the high oil content (38.5%, dry-weight basis) of its seeds. Subsequently, branch cuttings were collected from the donor tree and rooted by treating the cuttings with the rooting hormone indolebutyric acid (IBA) using either an aqueous solution of IBA (500 ppm) or a commercially available rooting powder. Dehydration of the cuttings was avoided by placing them in moistened rooting medium within a humid enclosed chamber. Rooting success varied from one collection event to another, which is normal for cuttings from mature trees. Typically 10% or more of the cuttings initiated root development within 3 to 4 weeks. Cuttings were rooted in Brisbane, Australia, as well as in Texas, U.S.A. These asexually propagated rooted cuttings remained true-to-type, and showed considerable resemblance among one another after accounting for differences such as variation in overall size of the cuttings.

Similar to *Pongamia* cultivars 'K140' (U.S. Patent Publ. No. 2015/0020251) and 'K606' (U.S. Patent Publ. No. 2015/0020252), 'K128b' has a strong tendency to produce regular crops of pods each year. Relative to other comparison cultivars, 'K128b' is unusual for its relatively small seeds (averaging 0.88 g) borne in correspondingly smaller pods. Seed oil content, at 38.5%, is similar to that of 'K606' (38.6%), but is substantially less than that of 'K140'. 'K128b' bears generally elliptical pods characterized by an apical tip that is less asymmetrically hooked than are pods of 'K140'. The spreading crown of 'K128b' lacks the tendency of 'K606' to bear upright branches and 'K128b' also lacks the tendency of 'K140' to bear pendulous shoots. Finally, some leaves (<10%) of 'K128b' bear a distinguishing anomaly in which one leaflet of the basal pair is replaced by two smaller and imperfectly formed leaflets.

BRIEF DESCRIPTION OF THE DRAWINGS

This new *Pongamia* tree is illustrated by the accompanying photographs, which show the tree's form, branches, foliage, leaves, trunk, pods, and seeds. The colors shown are as true as can be reasonably obtained by conventional photographic procedures.

DETAILED BOTANICAL DESCRIPTION

Figure 1:
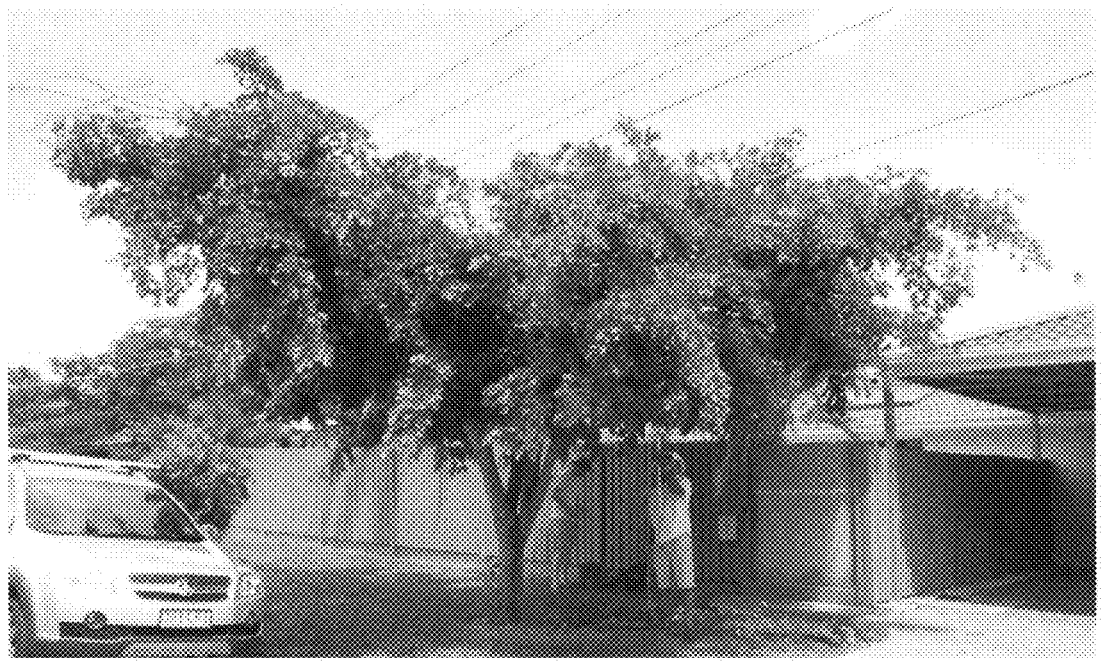
FIG. 1—shows an overview of 'K128b' as seen from the street. The spreading crown bears dense foliage. The top of the crown has been periodically pruned to keep foliage away from overhead power lines.
Figure 2:
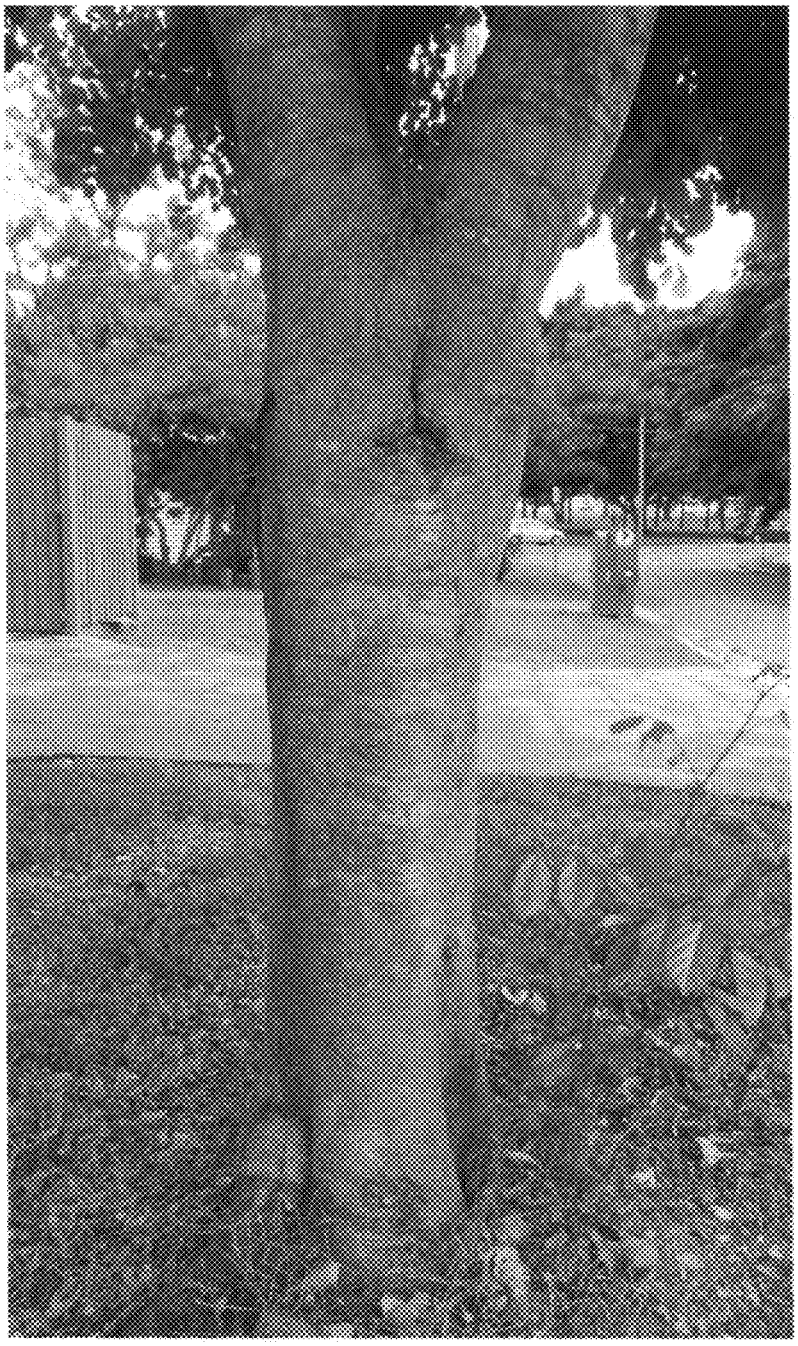
FIG. 2—shows a close-up of the smooth bark on the trunk, illustrating mottled patches of lighter and darker gray.
Figure 3:
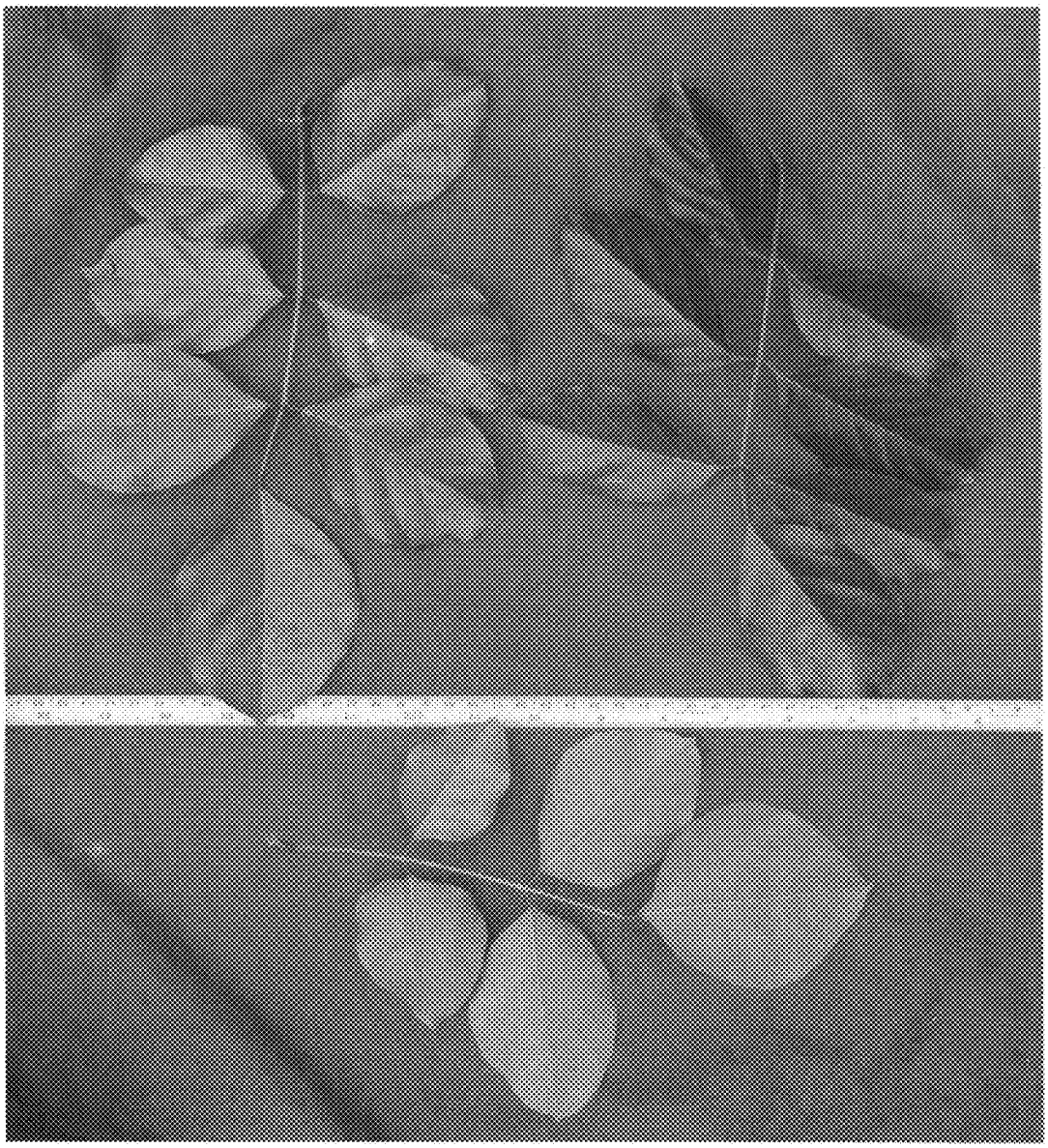
FIG. 3—shows pinnately compound leaves illustrating variation in color from lighter to darker green. The leaf at the bottom is oriented to show the underside. Compound leaves typically bear 5 to 7 leaflets.
Figure 4:
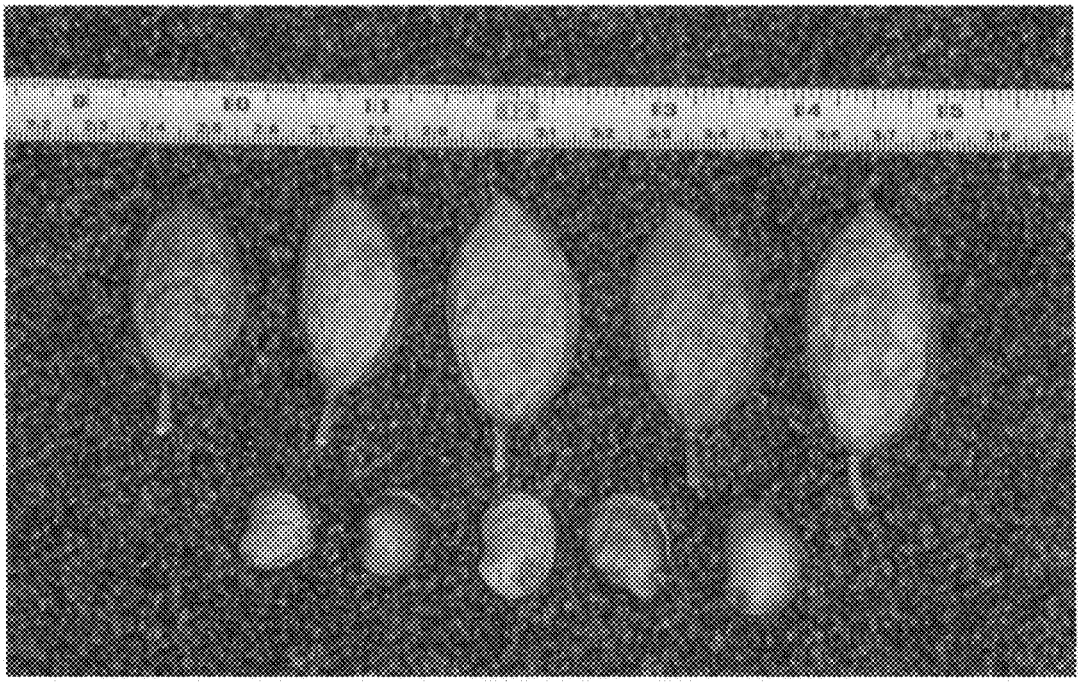
FIG. 4—shows pods (aligned in the top row) and seeds (bottom row). The pods are regularly elliptical in outline, but vary in size as shown. The brown to reddish-brown seeds also vary in size, with larger seeds being found in larger pods.
Figure 5:
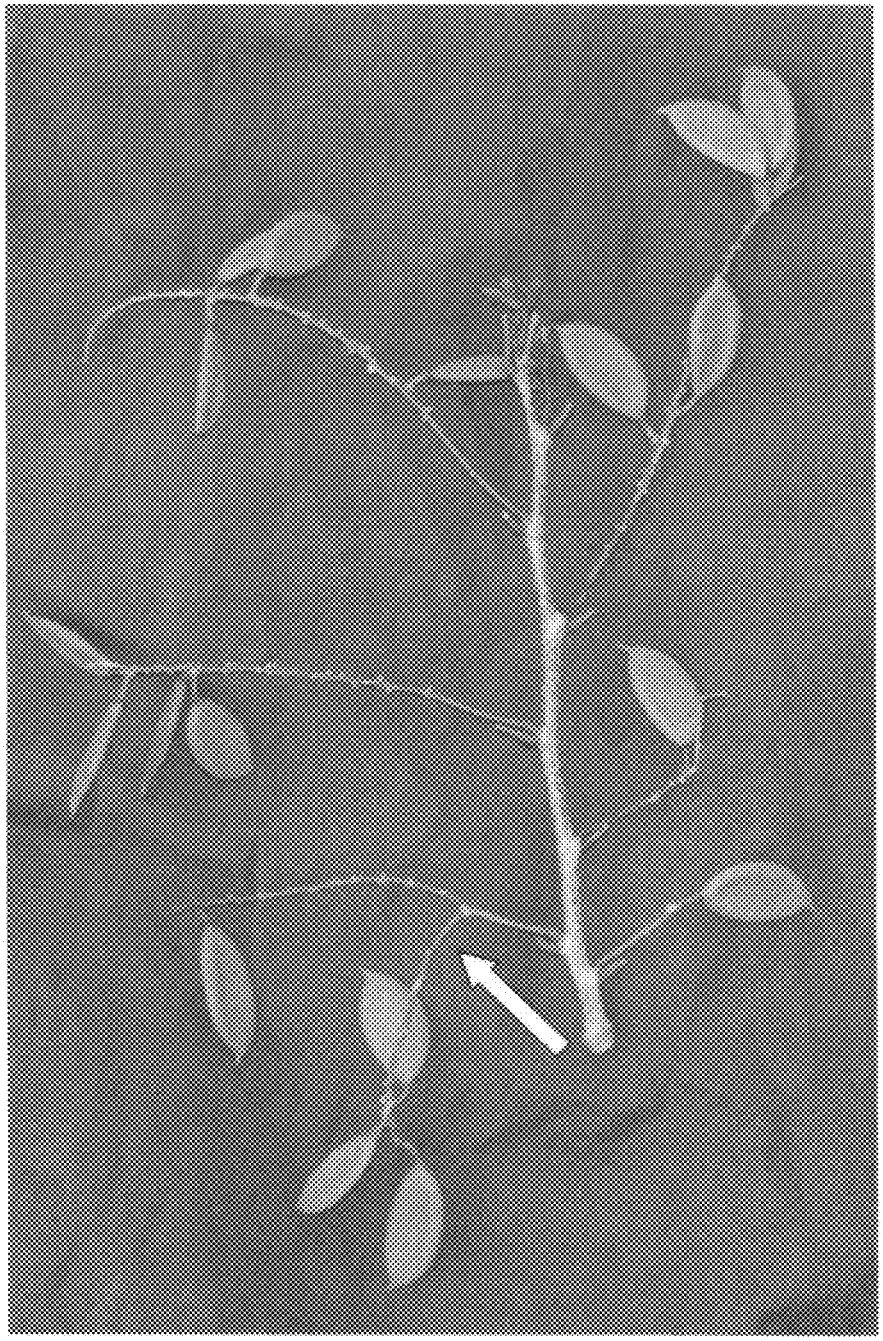
FIG. 5—shows a lateral branch representing the current year's growth flush. Leaves have been removed to illustrate six contiguous fertile nodes, each with an axillary rachis bearing one or more developing pods. The fruiting structure at lower left (arrow) illustrates a branched inflorescence.
Figure 6:
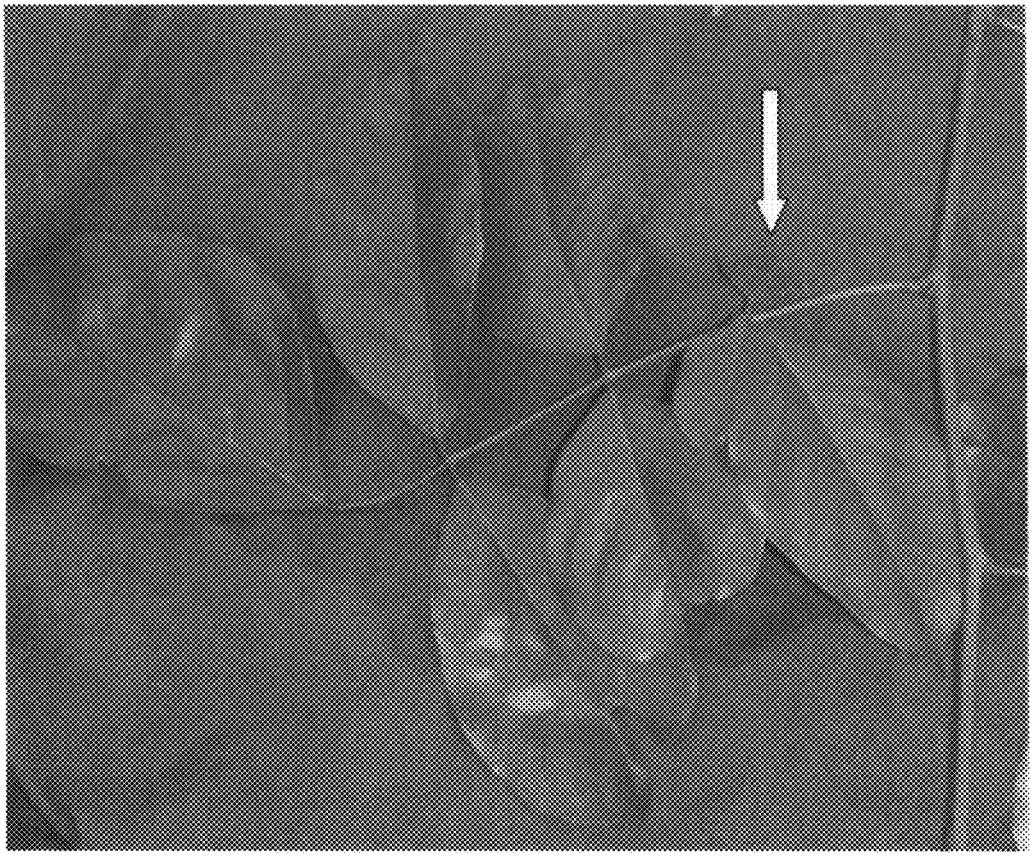
FIG. 6—shows a compound leaf illustrating an anomalous pair of small basal leaflets in place of the normal larger leaflet (arrow points to pair).
Figure 7:
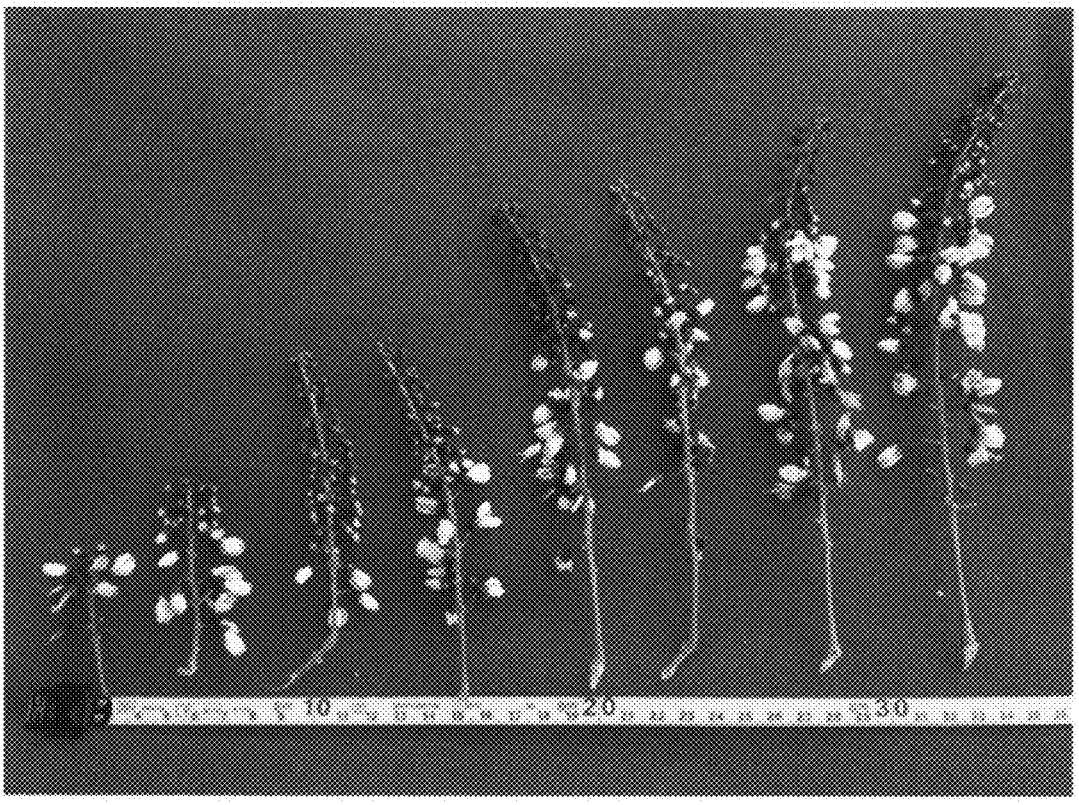
FIG. 7—shows inflorescences of various sizes and stages of maturity, illustrating acropetal development.

The following detailed description sets forth the distinctive characteristics of 'K128b'. Hereafter, standardized color designations refer to The Royal Horticultural Society (R.H.S.) Mini Colour Chart.

Classification:

*Family*.—Fabaceae.

*Botanical*.—*Pongamia pinnata* (L) Pierre; also called *Millettia pinnata* (L) Panigrahi, *Derris indica* (Lam.) Bennet, *Pongamia glabra* Vent, and *Cytisus pinnatus* (L).

*Common name*.—Pongam tree, or pongam oiltree.

*Cultivar name*.—'K128b'.

Plant description:

Tree:

*Size*.—Modest size and stature, 5.8 m in height. Crown diameter, measured at the drip-line in two dimensions, is 8.5×8.1 m.

*Trunk*.—The main stem is branched at a height of 1 m from the ground, and subsequently branches several more times shortly above. Diameter of the trunk at a height of 1 m above the ground is 28 cm. Tree crowns and trunks continue to grow as trees age. A small number of epicormic branches are visible along the trunk. A fully elongated epicormic shoot can range from approximately 30 to 86 cm in length, with a stem diameter of from about 3.5 to over 8 mm.

*Bark*.—Smooth, grey, with some lighter-color mottling. Faint lenticular scars are visible as horizontal striations.

*Form*.—Decurrent crown form with dense, compact foliage. Outer branches are arched downward without drooping. The crown of 'K128b' was pruned periodically as part of a maintenance routine to prevent unwanted interference with overhead utility lines, and to minimize encroachment into adjacent public spaces.

Branches: The three largest branches of 'K128b' are located on the main stem, just over 1 m from the ground. Their basal diameters are 18.5, 12.1, and 16.2 cm, and their color closely resembles the color of the main stem. Branch length is highly variable from year to year due to regular crown pruning, and thus is not a reliable defining characteristic of this tree.

*Branching habit*.—Many branched limbs. Growth and size of lateral branches are considerably less than that of the main branches. Many smaller branches occur higher in the crown.

*Buds and shoots*.—Terminal buds are absent. Young shoots emerge from naked lateral buds, with the most distal bud giving rise to a terminal shoot. Buds are hemispherical and range from 3.3 to 5.0 mm wide at their base. Buds protrude outward 1.7 to 3.5 mm from the stem and are between 1.2 to 1.5 mm thick. The typical bud color is strong yellowish green (RHS 144A) on younger shoots, and light olive (RHS 152B) on more mature shoots.

*Terminal shoots*.—The seasonal elongation of terminal shoots on main branches is considerable, ranging in length from about 22 to 55 cm and encompassing 8 to 18 leaf nodes. Stem diameters of terminal shoots range from 4.2 to 7.8 mm with an average of 5.2 mm.

*Lateral shoots*.—Seasonal elongation of lateral shoots is considerably shorter, ranging in length from 2 to 13 cm and bearing only 2 to 6 nodes. Diameters of lateral shoots range from 4.2 to 6.1 mm with a mean of 5.3 mm.

*Shoot and twig surfaces*.—Woody twigs have leaf scars that are 5.5 to 6.0 mm wide, showing traces of three vascular bundles. The youngest shoots are distinctly green and flexible, with no lenticels apparent to the naked eye. As shoots mature, their color shifts from green to tan and prominent lenticels become visible as raised light-colored corky circles approximately 1.5 mm in diameter.

Leaves: Pinnately compound leaves bear typically 5 or, more commonly 7 leaflets. Leaves are arranged alternately along the stem.

*Size and shape*.—The outline of a compound leaf is roughly oval, with a length of 14 to 32 cm (average 24 cm) and a width of 13 to 24 cm (average 20 cm).

*Leaflets*.—Blades of individual leaflets are oval to slightly ovate with cuspidate tips, acute bases, and entire margins. Blades of terminal leaflets range in width from 4.3 to 9.8 cm (average 7.8 cm) and in length from 5.3 to 11.8 cm (average 8.7 cm). The smallest leaflets on a leaf tend to be basal, ranging in width from 3.8 to 6.7 cm (average 4.8 cm) and in length from 4.2 to 10.2 cm (average 7.1 cm). A distinguishing anomaly on some leaves of 'K128b' is that a basal leaflet is replaced by two smaller and imperfectly formed leaflets. This was observed on a relatively small proportion (<10%) of leaves.

*Leaflet color, surface, and texture*.—Leaflets are glabrous on both abaxial and adaxial surfaces. Young leaves exhibit a strikingly glossy cuticle on their adaxial surface. The adaxial surface of a typical leaflet is dark green (RHS 136A), while the abaxial surface is deep yellowish green (RHS 141A) and is less glossy.

Newly expanded leaflets are a strong yellowish green (RHS 144A) on both the adaxial and abaxial surfaces. Leaflets turn a darker shade of green as they age and become increasingly sclerophyllous.

*Stipules*.—A pair of small stipules subtends the youngest leaves on a shoot. They remain for only a short duration before they dehisce.

Flowers and inflorescences: Hermaphroditic florets are borne on an indeterminate inflorescence.

*Inflorescence structure*.—Several florets are clustered into a fascicle node which are more-or-less evenly distributed along a rachis. The entire inflorescence is a pseudoraceme. Most inflorescences are unbranched, but some are branched. Infloresences are 6 to 23 cm in length and 3 to 4 cm in width, with a mean length of 17 cm and mean width of 3.1 cm.

*Position in crown*.—Inflorescences are borne in 4 to 6 basal leaf axils of the current year's vegetative flush, near the distal end of the prior year's shoot growth. An average unbranched inflorescence encompasses over 50 florets, and about 50% more on a branched inflorescence. Flower clusters tend to be most common towards the outer surface of the crown.

*Florets*.—Emerge acropetally from a fused ovoid calyx with entire margins and glabrous texture. The calyx has a typical depth of 3.3 mm and width of 4.5 mm, and is dark purple (RHS 83A) on both the inner and outer surfaces. Pedicels range from 5.6 to 8.3 mm in length and are 0.5 mm in diameter. Pedicels can be dark purple (RHS 83A) or light olive (RHS 152B), or a combination of both colors. Zygomorphic florets consist of 2 keel, 2 wing, and a standard (or banner) petal, and have a depth of 11.6 mm and a diameter of 10.0 mm. Banner petals are yellowish white (RHS 155D) on both surfaces, and often have a small colored patch (strong yellowish green, RHS 144A) just above the wings and keel on both surfaces. The banner apex is emarginate, and the base is rounded. Wing petals are typically 7.7 mm long and exhibit a very light purple (RHS 76B) coloration on both surfaces. Wing petal apices are obtuse, and bases are truncate.

*Flowering period*.—Tends to flower later relative to other *Pongamia* trees in the general area (early December in southeastern Queensland, Australia).

Fruits: Seed pods usually bear a single seed, infrequently two seeds.

*Shape and color*.—Developing fruits first appear as dark-green flattened pods, expanding in size into lighter green and eventually tan-colored woody pods.

*Crown distribution*.—Pods can occur throughout the crown, but are most prevalent towards the outer portions of the crown.

*Fruit clusters*.—Pods occur in clusters of 1 to 7, and are connected by the rachis of the inflorescence from which they developed.

*Dimensions*.—Pods range in size from 38 to 49 mm long, by 19 to 25 mm wide, by 8 to 11 mm thick, averaging 43.6×22.3×9.1 mm. Pods range in shape from oval to half-moon, with an acuminate tip, and average 1.26 g in weight. Fruits begin to ripen in late October (in southeastern Queensland, Australia), about 10 months after flowering.

Seeds: Typically borne singly in pods. Sometimes an aborted (and much smaller) seed occurs alongside a fully-formed seed.

*Seed coat*.—Seeds are covered by a thin seed coat that is beige to dark-brown.

*Seed size*.—Range in size from 16 to 20 mm long, by 12 to 15 mm wide, by 5 to 8 mm thick, averaging 18×14×6 mm. Average seed weight is 0.88 g.

*Seed oil*.—Oil content is higher than average, relative to other *Pongamia* trees, at 38.5% oil on a dry-weight basis.

*Nut crop*.—Regular bearer.

*Crop frequency*.—Most *Pongamia* trees rarely produce abundant nut crops across multiple years, instead bearing fruit biennially or less frequently. 'K128b' is unusual in that it bears fruit and seeds during most years.

*Ripening*.—Fruit ripening begins in late October and extends into December. If undisturbed, pods remain in the crown for several weeks after they ripen.

What is claimed is:

1. A new and distinct variety of *Pongamia pinnata* (L) Pierre tree called 'K128b' as illustrated and described herein.

* * * * *